United States Patent [19]

Rendenbach-Mueller et al.

[11] Patent Number: 5,100,914

[45] Date of Patent: Mar. 31, 1992

[54] ARYLALKOXYCOUMARINS

[75] Inventors: Beatrice Rendenbach-Mueller, Waldsee; Harald Weifenbach, Ludwigshafen; Jans-Juergen Teschendorf, Dudenhofen, all of Fed. Rep. of Germany

[73] Assignee: BASF Aktiengesellschaft, Ludwigshafen, Fed. Rep. of Germany

[21] Appl. No.: 414,307

[22] Filed: Sep. 29, 1989

[30] Foreign Application Priority Data

Oct. 13, 1988 [DE] Fed. Rep. of Germany ....... 3834861

[51] Int. Cl.$^5$ ................... C07D 311/16; A61K 31/37
[52] U.S. Cl. .................................. 514/457; 514/454; 549/289; 549/280
[58] Field of Search ................ 549/289, 280; 514/457, 514/454

[56] References Cited

U.S. PATENT DOCUMENTS

| | | | |
|---|---|---|---|
| 3,351,482 | 11/1967 | Raue et al. | 524/110 |
| 3,625,976 | 12/1971 | Theimer et al. | 549/289 |
| 3,712,947 | 1/1973 | Theimer et al. | 424/59 |
| 4,200,577 | 4/1980 | Buckle et al. | 514/547 |

FOREIGN PATENT DOCUMENTS 2805485 8/1978 Fed. Rep. of Germany .

OTHER PUBLICATIONS

Chemical Abstracts, No. 13 1-Pharmacology, pp. 634-635, C. Paul Blanchi.
Chemical Abstracts, No. 11, 1-Pharmacology, pp. 515-516, C. Paul Blanchi.
J. Chem. Soc., Chem. Commun. (16), 1264-1266 (CA 106:119499s).
Nippon Kagaku Kaishi (1), 96-99 (CA 82:149030k).
Phytochemistry 10 (12), 2965-2970.
Experientia 26 (11), 1281-1283.
J. Chem. Ecol. 13 (4), 917-924.
Chem. Pharm. Bull. 28 (12), 3662-2664.
Indian J. Chem., Sect. B, 25B (12), 1253-1254.
J. Indian Chem. Soc., 63 (4), 442-443.
Indian J. Chem., Sect. B, 25B (8), 862-865.
Curr. Sci. 53 (7), 369-371.
J. Agric. Food Chem. 34 (2), 185-188.

Primary Examiner—Jane T. Fan
Attorney, Agent, or Firm—Oblon, Spivak, McClelland, Maier & Neustadt

[57] ABSTRACT

Arylalkoxycoumarins of the general formula I

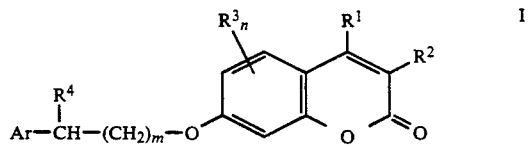

where $R^1$ and $R^2$ independently of one another are each hydrogen, lower alkyl, phenyl or halogen, or the two radicals together form an alkylene bridge of 3 to 5 carbon atoms, $R^3$ is lower alkyl or halogen, n is an integer of from 0 to 3, m is an integer of from 0 to 4, $R^4$ is hydrogen or lower alkyl and Ar is a phenyl ring which is monosubstituted to trisubstituted by halogen, $C_1$-$C_6$-alkyl or $C_1$-$C_6$-alkoxy or monosubstituted by nitro, cyano or trifluoromethyl or is a naphthyl ring, with the proviso that m is not 0 when Ar is unsubstituted phenyl, processes for their preparation, and drugs prepared therefrom.

3 Claims, No Drawings

ARYLALKOXYCOUMARINS

The present invention relates to novel arylalkoxycoumarins of the general formula I, which have useful therapeutic properties which are suitable in particular for the treatment of disorders of the central nervous system, and methods for their preparation.

The preparation and certain (microbicidal and UV-absorbing but non-pharmacological) properties of 7-benzyloxycoumarin and its derivatives phenylated or methylated in the 3- or 4-position are disclosed in, for example, the following literature:

J. Chem. Soc., Chem. Commun. (16), 1264-6 (CA 106: 119499s);
Nippon Kagaku Kaishi (1), 96-9 (CA 82:149030k);
Phytochemistry 10 (12), 2965-70;
Experientia 26 (11), 1281-3;
J. Chem. Ecol. 13 (4), 917-24;
Chem. Pharm. Bull. 28 (12), 3662-4;
Indian J. Chem., Sect. B, 25B (12), 1253-4;
J. Indian Chem. Soc., 63 (4), 442-3;
Indian J. Chem., Sect. B, 25B (8), 862-5;
Curr. Sci. 53 (7), 369-71; U.S. Pat. No. 3,712,947; U.S. Pat. No. 3,625,976; U.S. Pat. No. 3,351,482.

Furthermore, J. Agric. Food Chem. 34 (2), 185-188 discloses that 7-pentafluorophenylmethoxy-4-methylcoumarin has fungicidal activity.

It is an object of the present invention to provide novel therapeutic agents for the treatment of disorders of the central nervous system.

We have found that this object is achieved by the alkoxycoumarins of the general formula I a process for their preparation and the therapeutic agents.

In the general formula I

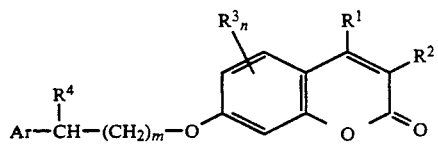

$R^1$ and $R^2$ may be identical or different and are each hydrogen, lower alkyl, phenyl or halogen, or $R^1$ and $R^2$ together form a chain of 3 to 5 carbon atoms, $R^3$ is lower alkyl or halogen, n is an integer of from 0 to 3, m is an integer of from 0 to 4, $R^4$ is hydrogen or lower alkyl and Ar is a phenyl ring which is monosubstituted to trisubstituted by halogen, $C_1$-$C_6$-alkyl or $C_1$-$C_6$-alkoxy or monosubstituted by nitro, cyano or trifluoromethyl or a combination of these substituents, or is a naphthyl ring, with the proviso that m is not 0 when Ar is unsubstituted phenyl.

Here, lower alkyl is $C_1$-$C_5$-alkyl and halogen is fluorine, bromine or, in particular, chlorine.

The compounds of the general formula I can be prepared, for example, by reacting a hydroxycoumarin of the formula II

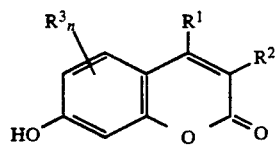

where $R^1$, $R^2$, $R^3$ and n have the abovementioned meanings, in a conventional manner with a compound of the formula III

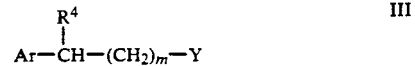

where $R^4$, m and Ar are as defined at the outset and Y is a nucleofugic leaving group, such as chlorine, bromine or $R^6SO_2O$. In this formula, $R^6$ is lower alkyl or is phenyl which is unsubstituted or substituted by lower alkyl or by halogen. The reaction can be carried out, as described in, for example, Houben-Weyl, Georg Thieme-Verlag, Stuttgart, 1965, Vol. 6/3, page 54 et seq., by heating the two components, preferably in the presence of an inert solvent, such as benzene, toluene, methylene chloride, acetone, lower alcohol, dimethylformamide or water, to a temperature between room temperature and the boiling point of the solvent used, if desired with the addition of a catalytic amount of sodium iodide. The acid liberated is generally trapped by adding a base, such as an alkali metal or alkaline earth metal hydroxide or carbonate or an amine such as pyridine or triethylamine. Instead of the hydroxycoumarins of the formula II, it is possible to react their alkali metal salts with the compounds of the formula III, preferably under anhydrous conditions in an aprotic solvent, such as ether, tetrahydrofuran, dimethylformamide, dimethoxyethane or dimethyl sulfoxide. Alkali metal hydrides or alkali metal alcoholates can be used as bases in these cases. Isolation and purification of the products are carried out by conventional methods, for example by recrystallization from a solvent, by extraction or by column chromatography.

The hydroxycoumarins of the general formula II can be prepared by known methods, as described in, for example, Elderfield R. C., Heterocyclic Compounds, John Wiley Publishers, New York 1951, Vol. 2, page 174 et seq., for example by condensation of a dihydroxybenzene of the formula IV

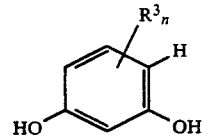

where $R^3$ and n have the abovementioned meanings, with a β-ketocarboxylic acid of the formula V

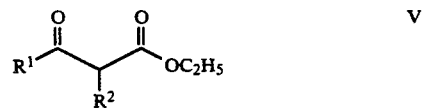

where $R^1$ and $R^2$ have the stated meanings in the presence of a condensing agent, such as sulfuric acid, phosphoric acid or aluminum chloride.

The aryl compounds of the general formula III are known and the majority of them are commercially available.

The compounds of the formula I have monoaminooxidase (MAO)-inhibiting activity. Because of this activity, the compounds of the formula I can be used for the treatment of disorders of the central nervous system, in particular neurodegenerative disorders and Parkinson's disease.

The MAO-inhibiting activity of the novel compounds can be determined using standard methods. For example, the determination of monoaminooxidases A and B was carried out in dilute rat brain homogenate to which 1. different concentrations of the test substances and 2. $^{14}$C-phenylethylamine or $^{14}$C-tryptamine in a concentration of 0.4 μmol/l had been added. This mixture was incubated for 20 minutes at 37° C. The reaction was then stopped by means of 0.1 normal HCl and the reaction products were determined after extraction in a toluene scintillator (PPO+POPOP in toluene). The blank value was determined in similar mixtures with an incubation time of t =0 min.

From the inhibitory values determined at the various inhibitor concentrations against the controls, the mean inhibitory concentration (IC50) was calculated by linear regression following logit-log transformation.

The activity determined in this manner for some novel compounds is shown in the Table below:

| Example | IC50 [μmol/l] MAO A | MAO B | MAO B MAO A |
|---|---|---|---|
| 1 | >10 | 0,007 | >1400 |
| 4 | >10 | 0,011 | >900 |
| 6 | >10 | 0,032 | >300 |
| 7 | >0,54 | 0,0011 | 490 |
| 8 | 0,39 | 0,00089 | 430 |
| 9 | 0,56 | 0,00087 | 640 |
| 10 | >10 | 0,0037 | >2700 |
| 12 | 2,1 | 0,00059 | 3500 |
| 19 | >10 | 0,0018 | >5500 |
| 20 | 0,3 | 0,0013 | 230 |
| 23 | >10 | 0,013 | >770 |
| 26 | >10 | 0,0018 | >5600 |
| 27 | >10 | 0,0047 | >2100 |
| 28 | >10 | 0,0028 | >3600 |
| 33 | >10 | 0,0043 | >2400 |
| 34 | 1,5 | 0,0035 | 430 |
| 35 | 1,2 | 0,0042 | 280 |
| 38 | >10 | 0,031 | >320 |
| Deprenyl | 2,0 | 0,0078 | 256 |
| Ro 19-6327 | >10 | 0,022 | >450 |

The novel compounds can be administered in a conventional manner, orally or parenterally (subcutaneously, intravenously, intramuscularly or intraperitoneally).

The dose depends on the age, condition and weight of the patient and on the route of administration. As a rule, the daily dose of active compound is from about 10 to 500 mg per patient per day in the case of oral administration and from about 1 to 50 mg per patient per day in the case of parenteral administration.

The novel compounds can be used in the conventional solid or liquid pharmaceutical forms, for example as tablets, film tablets, capsules, powders, granules, coated tablets, suppositories, solutions or sprays. These are prepared in a conventional manner and to do so the active compounds are mixed with the conventional pharmaceutical auxiliaries, such as tablet binders, fillers, preservatives, tablet disintegrants, flow regulators, plasticizers, wetting agents, dispersants, emulsifiers, solvents, retarding agents, antioxidants and/or propellants (cf. H. Sucker et al.: Pharmazeutische Technologie, Thieme-Verlag, Stuttgart, 1978). The administration forms thus obtained normally contain the active compound in a concentration of from 1 to 99% by weight.

EXAMPLE 1

3,4-Dimethyl-7-(4-isopropylphenyl)-methoxycoumarin 5.7 g of 7-hydroxy-3,4-dimethylcoumarin in 25 ml of dimethylformamide were added dropwise to a suspension of 1.05 g of NaH (80%) in 15 ml of dimethylformamide at room temperature. After 45 minutes, 5.05 g of 4-isopropylbenzyl chloride, dissolved in 20 ml of dimethylformamide, were added and the mixture was stirred overnight at room temperature. The reaction mixture was hydrolyzed with ice water, and the precipitated solid was filtered off under suction and recrystallized from methanol.

Yield: 4.3 g (45%); mp. 96° C.
$C_{21}H_{22}$ (322)
Calculated: 78.23 C, 6.88 H, 14.99 O;
Found: 78.0 C, 7.0 H, 14.8 O.

EXAMPLE 2

7-(4-Bromophenyl)-methoxy-3,4-dimethylcoumarin

A mixture of 5.0 g of 7-hydroxy-3,4-dimethylcoumarin, 5.4 g of 4-bromobenzyl chloride, 5.4 g of $K_2CO_3$ and 100 ml of acetone was stirred for 4 days at room temperature and evaporated down, and the residue was partitioned in $H_2O$/methylene chloride. After the organic phase had been separated off, extraction was carried out twice with methylene chloride, the combined organic phases were evaporated down and the residue was recrystallized from methanol.

Yield: 5.9 g (62%); mp. 153° C.
$C_{18}H_{15}BrO_3$ (359)
Calculated: 60.18 C, 4.21 H, 22.24 Br, 13.36 O;
Found: 60.1 C, 4.3 H, 22.2 Br, 13.5 O.

The following were prepared similarly to Example 1:

EXAMPLE 3

7-Benzyloxy-3,4-dimethylcoumarin

Yield: 61%; mp. 131°–135° C. (methanol)
$C_{18}H_{16}O_3$ (280)
Calculated:77.1 C, 5.71 H, 17.1 O;
Found: 77.1 C, 5.9 H, 17.0 O.

EXAMPLE 4

3,4-Dimethyl-7-(2-naphthyl)-methoxycoumarin

Yield: 62%; mp. 161°–164° C. (methanol)
$C_{22}H_{18}O_3$ (330)
Calculated: 79.50 C, 6.06 H, 14.44 O;
Found: 79.4 C, 5.8 H, 14.1 O.

EXAMPLE 5

3,4-Dimethyl-7-(1-naphthyl)-methoxycoumarin

Yield: 45%; mp. 186°–189° C. (methanol)
$C_{22}H_{18}O_3$ (330)
Calculated: 79.5 C, 6.06 H, 14.44 O;
Found: 79.3 C, 5.7 H. 14.5 O.

EXAMPLE 6

7-(4-tert-Butylphenyl)-methoxy-3,4-dimethylcoumarin

Yield: 47%; mp. 112°–113° C. (methanol)
$C_{22}H_{24}O_3$ (336)
Calculated: 78.54 C, 7.19 H, 14.27 O;
Found: 78.4 C, 7.5 H, 13.9 O.

EXAMPLE 7

3,4-Dimethyl-7-(2-methylphenyl)-methoxycoumarin

Yield: 81%; mp. 145° C. (methanol)
$C_{19}H_{18}O_3$ (294)
Calculated: 77.53 C, 6.16 H, 16.31 O;
Found: 77.6 C, 6.3 H, 16.3 O.

EXAMPLE 8

3,4-Dimethyl-7-(3-methylphenyl)-methoxycoumarin

Yield: 85%; mp. 114° C. (methanol)
$C_{19}H_{18}O_3$ (294)
Calculated: 77.53 C, 6.16 H, 16.31 O;
Found: 77.8 C, 6.1 H. 16.1 O.

EXAMPLE 9

3,4-Dimethyl-7-(4-methylphenyl)-methoxycoumarin

The reaction mixture was stirred for 3 hours at 60° C. and overnight at room temperature. The reaction mixture and working up were as described under Example 1.

Yield: 76%; mp.: 123° C. (methanol)
$C_{19}H_{18}O_3$ (294)
Calculated: 77.53 C, 6.16 H, 16.31 O;
Found: 77.6 C, 6.3 H, 16.2 O.

EXAMPLE 10

3,4-Dimethyl-7-(2,5-dimethylphenyl)-methoxycoumarin

The reaction was carried out as described under Example 9.

Yield: 82%; mp. 173°–175° C. (ethyl acetate)
$C_{20}H_{20}O_3$ (308)
Calculated: 77.90 C, 6.54 H, 15.56 O;
Found: 77.7 C, 6.6 H, 15.2 O.

EXAMPLE 11

3,4-Dimethyl-7-(2,4,6-trimethylphenyl)-methoxycoumarin

The reaction mixture was stirred for 3 hours at 60° C. and overnight at room temperature. The reaction mixture and working up were as described under Example 1.

Yield: 50%; mp. 175°–181° C. (ethyl acetate)
$C_{21}H_{22}O_3$ (322)
Calculated: 78.23 C, 6.88 H, 14.89 O;
Found: 78.1 C, 6.9 H, 14.7 O.

EXAMPLE 12

7-(4-Methoxyphenyl)-methoxy-3,4-dimethylcoumarin

The reaction was carried out as described under Example 9.

Yield: 66%; mp. 130°–132° C. (ethyl acetate)
$C_{19}H_{18}O_4$ (310)
Calculated: 73.53 C, 5.85 H, 20.62 O;
Found: 73.3 C, 5.9 H, 20.3 O.

EXAMPLE 13

3,4-Dimethyl-7-(4-nitrophenyl)-methoxycoumarin

The reaction mixture and procedure were as described under Example 1. The solid precipitated after the hydrolysis was filtered off under suction and extracted by boiling in succession with 500 ml of heptane and 500 ml of acetone, and the residue was dried under reduced pressure.

Yield: 25%; mp. 298°–299° C.
$C_{18}H_{25}NO_5$ (335)
Calculated: 66.46 C, 4.65 H, 4.51 N, 24.59 O;
Found: 66.2 C, 4.6 H, 4.5 N, 24.4 O.

EXAMPLE 14

7-(4-Fluorophenyl)-methoxy-3,4-dimethylcoumarin

Yield: 44%; mp. 142° C. (ethyl acetate)
$C_{18}H_{15}FO_3$ (298)
Calculated: 72.47 C, 5.07 H, 6.37 F, 16.09 O;
Found: 72.3 C, 5.2 H, 6.5 F, 16.0 O.

EXAMPLE 15

7-(4-Chlorophenyl)-methoxy-3,4-dimethylcoumarin

Yield: 30%; mp. 148° C. (ethyl acetate)
$C_{18}H_{15}ClO_3$ (315)
Calculated: 68.69 C, 4.8 H, 11.26 Cl, 15.25 O;
Found: 68.2 C, 4.9 H, 11.2 Cl, 15.5 O.

EXAMPLE 16

7-(4-Cyanophenyl)-methoxy-3,4-dimethylcoumarin

Yield: 67%; mp. 175°–176° C. (methanol)
$C_{19}H_{15}NO_3$ (305)
Calculated: 74.75 C, 4.96 H, 4.58 N, 15.7 O;
Found: 74.3 C, 4.9 H, 4.4 N, 16.2 O.

EXAMPLE 17

7-(3-Chlorophenyl)-methoxy-3,4-dimethylcoumarin

Yield: 74%; mp. 141° C. (ethyl acetate)
$C_{18}H_{15}ClO_3$ (315)
Calculated: 68.69 C, 4.8 H, 11.26 Cl, 15.25 O;
Found: 68.5 C, 4.9 H, 11.1 Cl, 15.2 O.

EXAMPLE 18

7-(3-Cyanophenyl)-methoxy-3,4-dimethylcoumarin

Yield: 48%; mp. 178°–183° C. (methanol)
$C_{19}H_{15}NO_3$ (305)
Calculated: 74.75 C, 4.96 H, 4.58 N, 15.7 O;
Found: 74.5 C, 5.1 H, 4.7 H, 15.5 O.

EXAMPLE 19

7-(4-Trifluoromethylphenyl)-methoxy-3,4-dimethylcoumarin

Yield: 62%; mp. 157°–160° C. (methanol)
$C_{19}H_{15}F_3O$ (348)
Calculated: 65.52 C, 4.34 H, 16.36 F, 13.78 O;
Found: 65.5 C, 4.4 H, 16.8 F, 13.3 O.

EXAMPLE 20

7-(3-Trifluoromethylphenyl)-methoxy-3,4-dimethylcoumarin

Yield: 56%; mp. 136°–138° C. (methanol)
$C_{19}H_{15}F_{3l}O$ (348)
Calculated: 65.52 C, 4.34 H, 16.36 F, 13.78 O;
Found: 65.4 C, 4.4 H, 16.9 F, 13.3 O.

EXAMPLE 21

3,4-Dimethyl-7-(2-phenylethoxy)-coumarin

The reaction mixture and procedure were as described under Example 1. The oily residue remaining after hydrolysis and decantation of the solvent was taken up in methylene chloride and the solution was washed with 2N NaOH solution and with water and dried over $Na_2SO_4$. The solid remaining after filtration and removal of the solvent was recrystallized from a little methanol.
Yield: 20%; mp. 116° C.
C19H18O3 (294)
Calculated: 77.53 C, 6.16 H, 16.31 O;
Found: 77.4 C, 6.3 H, 16.6 O.

EXAMPLE 22

3,4-Dimethyl-7-[1-(4-isopropylphenyl)]-ethoxycoumarin

The reaction mixture and procedure were as described under Example 1. After the hydrolysis, the mixture was extracted with methyl tert-butyl ether, the organic phase was washed with H2O and dried, and the solid remaining after evaporation was recrystallized from methanol.
Yield: 20%; mp. 152°-153° C.

EXAMPLE 23

6-Ethyl-3,4-dimethyl-7-(2-phenyl)-ethoxycoumarin
Yield: 35%; mp. 123° C. (methanol)
C21H22O3 (322)
Calculated: 78.23 C, 6.88 H, 14.99 O;
Found: 78.5 H C, 7.2 H, 14.4 O.

EXAMPLE 24

3,4,8-Trimethyl-7-(4-isopropylphenyl)-methoxycoumarin
Yield: 49%; mp. 172° C. (methanol)
C22H24O3 (336)
Calculated: 78.54 C, 7.19 H, 14.27 O;
Found: 78.4 C, 7.4 H, 14.2 O.

EXAMPLE 25

6-Ethyl-3,4-dimethyl-7-(4-isopropylphenyl)-methoxycoumarin
Yield: 65%; mp. 129° C. (methanol)
C23H26O3 (350)
Calculated: 78.85 C, 7.42 H, 13.71 O;
Found: 78.6 C, 7.6 H, 13.6 O.

EXAMPLE 26

7-(4-Isopropylphenyl)-methoxycoumarin
Yield: 46%; mp. 127° C. (methanol)
C19H18O3 (294)
Calculated: 77.53 C, 6.16 H, 16.31 O;
Found: 77.3 C, 6.2 H, 16.3 O.

EXAMPLE 27

4-Methyl-7-(4-isopropylphenyl)-methoxycoumarin
Yield: 46%; mp. 156° C. (methanol)
C20H20O3 (308)
Calculated: 77.90 C, 6.54 H, 15.56 O;
Found: 77.9 C, 6.7 H, 15.6 O.

EXAMPLE 28

3-Methyl-7-(4-isopropylphenyl)-methoxycoumarin
Yield: 42%; mp. 129° C. (methanol)
C20H20O3 (308)
Calculated: 77.90 C, 6.54 H, 15.56 O;
Found. 77.4 C, 6.6 H, 15.4 O.

EXAMPLE 29

3-Ethyl-4-methyl-7-(4-isopropylphenyl)-methoxycoumarin
Yield: 64%; mp. 115° C. (methanol)
C20H24O3 (336)
Calculated: 78.54 C, 7.19 H, 14.27 O;
Found: 78.6 C, 7.3 H, 14.3 O.

EXAMPLE 30

4-Ethyl-3-methyl-7-(4-isopropylphenyl)-methoxycoumarin
Yield: %; mp. 83° C. (methanol)

EXAMPLE 31

3,4-Tetramethylene-7-(4-isopropylphenyl)-methoxycoumarin
Yield: 39%; mp. 129° C. (methanol)
C23H24O3 (348)
Calculated: 79.28 C, 6.94 H, 13.77 O;
Found: 79.5 C, 7.0 H, 13.7 O.

EXAMPLE 32

4-Phenyl-7-(4-isopropylphenyl)-methoxycoumarin

The reaction mixture and procedure was as described under Example 1. After the hydrolysis, the mixture was extracted with methyl tert-butyl ether and the organic phase was dried and evaporated down.
Yield: 48%; mp. 85.5° C. (methanol)

EXAMPLE 33

3-Chloro-4-methyl-7-(4-isopropylphenyl)-methoxycoumarin
Yield: 16%; mp. 124° C. (methanol)
C20H19ClO3 (343)
Calculated: 70.07 C, 5.54 H, 14.01 O;
Found: 70.5 C, 5.8 H, 13.7 O.

EXAMPLE 34

7-(3-Phenylpropoxy)-counarin

The preparation was carried out as described under Example 21.
Yield: 43%; mp. 124°-126° C. (methanol)

EXAMPLE 35

3,4-Dimethyl-7-(3-phenylpropoxy)-coumarin

The procedure was carried out as described under Example 21.
Yield: 51%; mp. 104° C. (methanol)
C20H20O3 (308)
Calculated: 77.90 C, 6.54 H, 15.56 O;
Found: 77.8 C, 6.6 H, 15.4 O.

EXAMPLE 36

7-(5-Phenylpentoxy)-coumarin

The procedure was carried out as described under Example 21.
Yield: 37%; mp. 103° C. (methanol)

EXAMPLE 37

3,4-Dimethyl-7-(5-phenylpentoxy)-coumarin

The procedure was carried out as described under Example 21.
Yield: 32%; mp. 101° C. (methanol)

EXAMPLE 38

6-Chloro-3,4-dimethyl-7-(4-isopropylphenyl)-methoxycoumarin

The procedure and working up were carried out similarly to Example 2.

Yield: 47%; mp. 168° C. (ethyl acetate)

$C_{21}H_{21}ClO_3$ (357)

Calculated: 70.68 C, 5.93 H, 9.94 Cl, 13.45 O;

Found: 70.3 C, 6.0 H, 9.8 Cl, 13.5 O.

Examples of pharmaceutical administration forms:

(A) Tablets having the following composition were obtained by pressing on a tabletting press in a conventional manner:

40 mg of the substance of Example 1
120 mg of corn starch
13.5 mg of gelatine
45 mg of lactose
2.25 mg of Aerosil ® (chemically pure submicroscopic silica)
6.75 mg of potato starch (as a 6% strength paste)

(B) 20 mg of the substance of Example 3
60 mg of core material
60 mg of sugar-coating material The core material consists of 9 parts of corn starch, 3 parts of lactose and 1 part of Luviskol ® VA 64 (60:40 vinylpyrrolidone/vinyl acetate copolymer, cf. Pharm. Ind. 1962 586). The sugar-coating material consists of 5 parts of sucrose, 2 parts of corn starch, 2 parts of calcium carbonate and 1 part of talc. The coated tablets prepared in this manner are then provided with a coating which is resistant to gastric juice.

We claim:

1. An arylalkoxycoumarin of the formula I

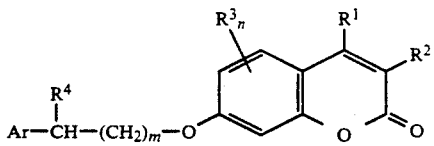

where $R^1$ and $R^2$ indepenently of one another are each lower alkyl, phenyl or halogen, or the two groups together form an alkylene bridge of 3 to 5 carbon atoms, $R^3$ is lower alkyl or halogen, n is an integer of from 0 to 3, m is an integer of from 0 to 4, $R^4$ is hydrogen or lower alkyl and Ar is a phenyl ring which is monosubstituted to trisubstituted by halogen or $C_1$-$C_6$-alkoxy, disubstituted to trisubstituted by $C_1$-$C_6$-alkyl, or monosubstituted by nitro, cyano or trifluoromethyl.

2. An oral therapeutic composition for treatment of central nervous system disorders by inhibition of monoamine oxidase which contains, as the active compound, from 10 to 500 g, per dose, of a compound of the formula I as claimed in claim 1, in addition to conventional pharmaceutical auxiliaries.

3. A parenteral therapeutic composition for treatment of central nervous system disorders by inhibition of monoamine oxidase which contains, as the active compound, from 1 to 50 mg, per dose, of a compound of the formula I as claimed in claim 1, in addition to conventional pharmaceutical auxiliaries.

* * * * *

UNITED STATES PATENT AND TRADEMARK OFFICE
CERTIFICATE OF CORRECTION

PATENT NO. : 5,100,914
DATED : March 31, 1992
INVENTOR(S) : Beatrice Rendenbach-Mueller et al.

It is certified that error appears in the above-identified patent and that said Letters Patent is hereby corrected as shown below:

On the Title page, item [75], the third inventor's name should be

--Hans-Juergen Teschendorf--.

Signed and Sealed this

Eighth Day of June, 1993

Attest:

MICHAEL K. KIRK

Attesting Officer

Acting Commissioner of Patents and Trademarks